United States Patent
Dastmalchi et al.

(10) Patent No.: US 11,195,213 B2
(45) Date of Patent: Dec. 7, 2021

(54) METHOD OF OPTIMIZING PATIENT-RELATED OUTCOMES

(71) Applicant: Apixio, Inc., San Mateo, CA (US)

(72) Inventors: Shahram Shawn Dastmalchi, San Ramon, CA (US); Vishnuvyas Sethumadhavan, Mountain View, CA (US); Mary Ellen Campana, San Mateo, CA (US); Robert Derward Rogers, Pleasanton, CA (US); Imran N. Chaudhri, Potomac, MD (US)

(73) Assignee: APIXIO, INC., San Mateo, CA (US)

( * ) Notice: Subject to any disclaimer, the term of this patent is extended or adjusted under 35 U.S.C. 154(b) by 992 days.

(21) Appl. No.: 13/801,947

(22) Filed: Mar. 13, 2013

(65) Prior Publication Data
US 2013/0275153 A1  Oct. 17, 2013

Related U.S. Application Data

(63) Continuation-in-part of application No. 13/223,228, filed on Aug. 31, 2011, now Pat. No. 10,176,541.
(Continued)

(51) Int. Cl.
*G06Q 30/02* (2012.01)
*G06Q 40/08* (2012.01)
(Continued)

(52) U.S. Cl.
CPC ......... *G06Q 30/0283* (2013.01); *G06Q 40/08* (2013.01); *G16H 10/20* (2018.01); *G16H 10/60* (2018.01); *G16H 50/70* (2018.01)

(58) Field of Classification Search
CPC .... G06Q 50/22; G06Q 50/24; G06Q 30/0283; G06Q 40/08; G06F 19/328; G06C 30/0283; G16H 10/20; G16H 10/60; G16H 50/70
(Continued)

(56) References Cited

U.S. PATENT DOCUMENTS

| 5,164,899 A | 11/1992 | Sobotka et al. |
| 5,307,262 A | 4/1994 | Ertel |

(Continued)

FOREIGN PATENT DOCUMENTS

| CA | 2216681 A1 * | 3/1998 | ............. G16H 50/50 |
| CA | 2722773 A1 * | 11/2009 | ............. G16H 50/20 |

(Continued)

OTHER PUBLICATIONS

Korean Intellectual Property Office, ISA, "International Search Report and Written Opinion" in PCT Application No. PCT/US2013/038541, dated Aug. 19, 2013, 9 pages.
(Continued)

*Primary Examiner* — John B King
(74) *Attorney, Agent, or Firm* — Armstrong Teasdale LLP

(57) ABSTRACT

A medical information navigation engine ("MINE") is provided. In some embodiments, the system computes a current patient encounter vector for a current patient encounter, and then an optimal patient encounter vector is computed by assuming a best case patient encounter in accordance with the organizational objectives. The system is then able to compute the difference between the best case encounter and the current patient encounter. This difference is used to compute a corresponding payoff using an intelligent matrix.

10 Claims, 13 Drawing Sheets

Identify Association or Correlated States Between (Among) Patients
360

Patient 1

Patient 2

Related U.S. Application Data

(60) Provisional application No. 61/639,805, filed on Apr. 27, 2012, provisional application No. 61/379,228, filed on Sep. 1, 2010.

(51) Int. Cl.
*G16H 10/20* (2018.01)
*G16H 10/60* (2018.01)
*G16H 50/70* (2018.01)

(58) Field of Classification Search
USPC .............................................. 705/2
See application file for complete search history.

(56) References Cited

U.S. PATENT DOCUMENTS

| | | | |
|---|---|---|---|
| 5,544,044 A | 8/1996 | Leatherman | |
| 5,875,263 A | 2/1999 | Froessl | |
| 5,924,074 A * | 7/1999 | Evans | G16H 20/10 705/3 |
| 6,076,088 A | 6/2000 | Paik et al. | |
| 6,151,581 A * | 11/2000 | Kraftson | G06Q 40/08 705/3 |
| 6,209,095 B1 | 3/2001 | Anderson et al. | |
| 6,266,645 B1 | 7/2001 | Simpson | |
| 6,336,108 B1 | 1/2002 | Thiesson et al. | |
| 6,341,265 B1 | 1/2002 | Provost et al. | |
| 6,505,196 B2 | 1/2003 | Drucker et al. | |
| 6,601,055 B1 * | 7/2003 | Roberts | G06F 19/345 600/300 |
| 6,675,044 B2 * | 1/2004 | Chen | A61B 5/0006 600/523 |
| 6,874,085 B1 | 3/2005 | Koo et al. | |
| 7,321,861 B1 | 1/2008 | Oon | |
| 7,702,524 B1 | 4/2010 | Whibbs et al. | |
| 7,925,678 B2 | 4/2011 | Botros et al. | |
| 8,254,681 B1 | 8/2012 | Poncin et al. | |
| 8,380,530 B2 | 2/2013 | Marshall | |
| 8,620,078 B1 | 12/2013 | Chapleau et al. | |
| 8,977,076 B2 | 3/2015 | Samadani et al. | |
| 9,495,515 B1 | 11/2016 | Kennedy et al. | |
| 10,628,553 B1 | 4/2020 | Murrish et al. | |
| 2001/0042080 A1 | 11/2001 | Ross | |
| 2002/0007284 A1 | 1/2002 | Schurenberg et al. | |
| 2002/0010679 A1 | 1/2002 | Felsher | |
| 2002/0103834 A1 | 8/2002 | Thompson et al. | |
| 2002/0120466 A1 | 8/2002 | Finn | |
| 2002/0143562 A1 * | 10/2002 | Lawrence | 705/1 |
| 2002/0188182 A1 | 12/2002 | Haines et al. | |
| 2003/0004748 A1 | 1/2003 | Coleman et al. | |
| 2003/0084043 A1 | 5/2003 | Acharya et al. | |
| 2003/0120458 A1 | 6/2003 | Rao et al. | |
| 2003/0120640 A1 | 6/2003 | Ohta et al. | |
| 2003/0187950 A1 * | 10/2003 | Rising, III | G06F 16/40 709/218 |
| 2003/0220915 A1 | 11/2003 | Fagan et al. | |
| 2003/0229510 A1 | 12/2003 | Kerr | |
| 2004/0073458 A1 | 4/2004 | Jensen | |
| 2004/0122702 A1 | 6/2004 | Sabol et al. | |
| 2004/0172297 A1 | 9/2004 | Rao et al. | |
| 2004/0220895 A1 | 11/2004 | Carus et al. | |
| 2004/0249667 A1 | 12/2004 | Oon | |
| 2005/0043986 A1 | 2/2005 | McConnell et al. | |
| 2005/0251422 A1 | 5/2005 | Wolfman | |
| 2005/0137912 A1 | 6/2005 | Rao et al. | |
| 2005/0138017 A1 | 6/2005 | Keen et al. | |
| 2005/0154690 A1 | 7/2005 | Nitta et al. | |
| 2005/0182659 A1 | 8/2005 | Huttin | |
| 2005/0192792 A1 | 9/2005 | Carus et al. | |
| 2005/0203773 A1 | 9/2005 | Soto et al. | |
| 2005/0228593 A1 | 10/2005 | Jones | |
| 2005/0240439 A1 | 10/2005 | Covit et al. | |
| 2005/0283062 A1 | 12/2005 | Hoffman et al. | |
| 2006/0026036 A1 * | 2/2006 | Mahmood | 705/2 |
| 2006/0026525 A1 | 2/2006 | Fischer et al. | |
| 2006/0036619 A1 * | 2/2006 | Fuerst | G16H 50/70 |
| 2006/0047669 A1 * | 3/2006 | Durrence | G06F 16/93 |
| 2006/0053098 A1 | 3/2006 | Gardner et al. | |
| 2006/0112050 A1 | 5/2006 | Miikkulainen et al. | |
| 2006/0129435 A1 | 6/2006 | Smitherman et al. | |
| 2006/0179016 A1 | 8/2006 | Forman et al. | |
| 2006/0184475 A1 | 8/2006 | Krishnan et al. | |
| 2006/0241978 A1 | 10/2006 | Yoshii | |
| 2006/0265249 A1 * | 11/2006 | Follis | G16H 15/00 705/3 |
| 2006/0265251 A1 | 11/2006 | Patterson | |
| 2006/0265253 A1 | 11/2006 | Rao et al. | |
| 2007/0016450 A1 | 1/2007 | Bhora et al. | |
| 2007/0055545 A1 | 3/2007 | Maughan et al. | |
| 2007/0055552 A1 | 3/2007 | St. Clair et al. | |
| 2007/0061348 A1 | 3/2007 | Holland et al. | |
| 2007/0061393 A1 | 3/2007 | Moore | |
| 2007/0078680 A1 * | 4/2007 | Wennberg | G06F 19/327 705/2 |
| 2007/0083390 A1 * | 4/2007 | Gorup et al. | 705/2 |
| 2007/0088559 A1 | 4/2007 | Kim | |
| 2007/0106754 A1 | 5/2007 | Moore | |
| 2007/0118399 A1 | 5/2007 | Avinash et al. | |
| 2007/0162308 A1 | 7/2007 | Peters | |
| 2007/0168461 A1 | 7/2007 | Moore | |
| 2007/0192143 A1 | 8/2007 | Krishnan et al. | |
| 2007/0219829 A1 | 9/2007 | Kay | |
| 2007/0226211 A1 | 9/2007 | Heinze et al. | |
| 2008/0040151 A1 | 2/2008 | Moore | |
| 2008/0052255 A1 | 2/2008 | Fan et al. | |
| 2008/0077443 A1 | 3/2008 | Singer | |
| 2008/0091633 A1 * | 4/2008 | Rappaport | G06N 5/022 706/50 |
| 2008/0097936 A1 | 4/2008 | Schmidtler et al. | |
| 2008/0120296 A1 | 5/2008 | Kariathungal et al. | |
| 2008/0147441 A1 * | 6/2008 | Kil | 705/2 |
| 2008/0195570 A1 | 8/2008 | Alsafadi et al. | |
| 2008/0208630 A1 | 8/2008 | Fors et al. | |
| 2008/0256181 A1 | 10/2008 | Morita et al. | |
| 2008/0263048 A1 | 10/2008 | Wise | |
| 2008/0270120 A1 | 10/2008 | Pestian et al. | |
| 2008/0270340 A1 * | 10/2008 | Abrams | G06F 16/00 |
| 2008/0287746 A1 | 11/2008 | Reisman | |
| 2008/0288292 A1 | 11/2008 | Bi et al. | |
| 2008/0320029 A1 | 12/2008 | Stivoric et al. | |
| 2009/0024615 A1 * | 1/2009 | Pedro | G06F 16/367 |
| 2009/0048877 A1 | 2/2009 | Binns et al. | |
| 2009/0070103 A1 * | 3/2009 | Beggelman | G06F 40/20 704/9 |
| 2009/0076839 A1 | 3/2009 | Abraham-Fuchs et al. | |
| 2009/0099876 A1 | 4/2009 | Whitman | |
| 2009/0110287 A1 | 4/2009 | Bates et al. | |
| 2009/0112882 A1 | 4/2009 | Maresh | G16H 10/60 |
| 2009/0125246 A1 | 5/2009 | Laza | |
| 2009/0136102 A1 * | 5/2009 | Kimpe | G06T 7/32 382/128 |
| 2009/0138287 A1 | 5/2009 | Hermann, Jr. | |
| 2009/0198517 A1 | 8/2009 | Ruben et al. | |
| 2009/0216696 A1 | 8/2009 | Downs et al. | |
| 2009/0220175 A1 | 9/2009 | Tzadok et al. | |
| 2009/0238625 A1 | 9/2009 | Ming et al. | |
| 2009/0259487 A1 | 10/2009 | Rao et al. | |
| 2009/0265189 A1 | 10/2009 | Bartholomew et al. | |
| 2009/0271221 A1 * | 10/2009 | Aridi | G16H 10/65 705/3 |
| 2009/0287504 A1 | 11/2009 | Benjamin et al. | |
| 2009/0326981 A1 | 12/2009 | Karkanias et al. | |
| 2010/0036680 A1 | 2/2010 | Familant | |
| 2010/0117799 A1 | 5/2010 | Dormer et al. | |
| 2010/0131299 A1 | 5/2010 | Hasan et al. | |
| 2010/0131438 A1 | 5/2010 | Pandya et al. | |
| 2010/0131482 A1 | 5/2010 | Linthicum et al. | |
| 2010/0145723 A1 | 6/2010 | Hudson et al. | |
| 2010/0169123 A1 | 7/2010 | Maus et al. | |
| 2010/0174579 A1 | 7/2010 | Hughes | |
| 2010/0179827 A1 | 7/2010 | McCallie, Jr. et al. | |
| 2010/0185496 A1 * | 7/2010 | Hahn | G06Q 30/0204 705/7.33 |

(56) References Cited

U.S. PATENT DOCUMENTS

| | | |
|---|---|---|
| 2010/0228721 A1 | 9/2010 | Mok et al. |
| 2010/0274584 A1 | 10/2010 | Kim |
| 2010/0281036 A1 | 11/2010 | Inoue et al. |
| 2010/0310172 A1 | 12/2010 | Natarajan et al. |
| 2010/0324927 A1 | 12/2010 | Tinsley |
| 2010/0324936 A1 | 12/2010 | Vishnubhatla et al. |
| 2011/0004588 A1 | 1/2011 | Leitersdorf et al. |
| 2011/0072002 A1 | 3/2011 | Kirkby et al. |
| 2011/0077972 A1 | 3/2011 | Breitenstein et al. |
| 2011/0078145 A1 | 3/2011 | Chung et al. |
| 2011/0093293 A1 | 4/2011 | G. N. et al. |
| 2011/0093334 A1 | 4/2011 | Wood |
| 2011/0117799 A1 | 5/2011 | Harada et al. |
| 2011/0119089 A1 | 5/2011 | Carlisle |
| 2011/0131062 A1 | 6/2011 | Menschik et al. |
| 2011/0196702 A1 | 8/2011 | Salouk et al. |
| 2011/0225001 A1 | 9/2011 | Shen |
| 2011/0251989 A1 | 10/2011 | Kraaij et al. |
| 2011/0258001 A1 | 10/2011 | Green et al. |
| 2011/0264665 A1 | 10/2011 | Mital et al. |
| 2011/0270632 A1 | 11/2011 | Manning et al. |
| 2011/0295775 A1 | 12/2011 | Wang et al. |
| 2012/0041772 A1* | 2/2012 | Ebadollahi .......... G06F 19/3443 705/2 |
| 2012/0060216 A1 | 3/2012 | Chaudhri et al. |
| 2012/0066017 A1 | 3/2012 | Siegel |
| 2012/0089412 A1 | 4/2012 | Bardy et al. |
| 2012/0089606 A1 | 4/2012 | Eshwar et al. |
| 2012/0110016 A1 | 5/2012 | Phillips |
| 2012/0166212 A1 | 6/2012 | Campbell |
| 2012/0215578 A1 | 8/2012 | Swierz et al. |
| 2012/0239671 A1 | 9/2012 | Chaudhri et al. |
| 2012/0278102 A1 | 11/2012 | Johnson |
| 2012/0284056 A1 | 11/2012 | Hofstetter |
| 2012/0303378 A1 | 11/2012 | Lieberman |
| 2013/0007020 A1 | 1/2013 | Basu et al. |
| 2013/0046529 A1 | 2/2013 | Grain et al. |
| 2013/0124523 A1 | 5/2013 | Rogers et al. |
| 2013/0159023 A1 | 6/2013 | Srinivas et al. |
| 2013/0166317 A1* | 6/2013 | Beardall ................ G16H 40/63 705/2 |
| 2013/0231956 A1* | 9/2013 | Chaudhri et al. .................. 705/3 |
| 2013/0238349 A1 | 9/2013 | Sethumadhavan et al. |
| 2013/0291060 A1 | 10/2013 | Moore |
| 2013/0297536 A1 | 11/2013 | Almosni et al. |
| 2013/0332194 A1 | 12/2013 | DAuria et al. |
| 2013/0332199 A1 | 12/2013 | Freiwat et al. |
| 2014/0012738 A1 | 1/2014 | Woo |
| 2014/0046697 A1 | 2/2014 | Rogers et al. |
| 2014/0136559 A1 | 5/2014 | Kottaram |
| 2014/0257842 A1 | 9/2014 | Heinze et al. |
| 2014/0278832 A1 | 9/2014 | Glavina et al. |
| 2015/0019463 A1 | 1/2015 | Simard et al. |
| 2015/0066537 A1 | 3/2015 | Sheffer et al. |
| 2015/0066539 A1 | 3/2015 | Sheffer et al. |
| 2016/0048643 A1 | 2/2016 | Woods et al. |
| 2017/0132314 A1 | 5/2017 | Liu et al. |

FOREIGN PATENT DOCUMENTS

| | | | |
|---|---|---|---|
| CN | 1529481 A * | 9/2004 | |
| EP | 0791203 B1 * | 4/1998 | ............ G16H 10/65 |
| JP | 09135816 A | 5/1997 | |
| JP | 11219403 A | 8/1999 | |
| JP | 4471736 B2 | 6/2010 | |
| JP | 2010134946 A | 6/2010 | |
| KR | 20010002074 A * | 1/2001 | |
| KR | 100750071 B1 | 8/2007 | |
| KR | 1020120004749 B1 | 1/2012 | |

OTHER PUBLICATIONS

Korean Intellectual Property Office, ISA, "International Search Report and Written Opinion" in PCT Application No. PCT/US2012/053182, dated Mar. 18, 2013, 12 pages.

Lynunn, How Elasticsearch calculates significant terms, Jun. 10, 2015, ComperioSearch (Year: 2015).

Bentkus et al., "Confidence Bounds for a Parameter" Sep. 2001 Mathematics Subject Classification.

Feature Selection, Apr. 5, 2016, Wikipedia (Year: 2016).

Lemeshow et al., Searching one or two databases was insufficient for meta-analysis of observational studies, 7 pages (Year: 2005).

Natarajan et al., "An Analysis of Clinical Queries in an Electronic Health Record Search Utility" Int. J Med Inforamtics, Jul. 2010.

Rector et al., "Medical-Concept Models and Medical Records: An approach based on GALEN and PEN PAD" Journal of the American Medical Informatics Association, vol. 2 No. 1 Jan./Feb. 1995.

Roque et al., "Using Electronic Patient Records to Discover Disease Correlations and Stratify Patient Cohorts" PLoS Computational Biology, Aug. 2011, vol. 7, Issue 8 el 002141.

The Statistics Calculator, StatPac; Dec. 17, 2003, available from: http://web.archive.org/web/20031217141819/http://statpac.com/statisticscalculator/percents.htm.

* cited by examiner

Construction of Patient Timeline 300

Patient state timeline is constructed by ordering individual states in time order.

Addition of Impact Measure, V(t), to Patient State Timeline 340

Identify Association or Correlated States
Between (Among) Patients
360

Patient 1

Patient 2

380

Patient 1

Patient 2

Composite Trajectory/ Aggregated Timeline

APIXIO

Coding Opportunity 0.353    John Sample    HCC 55    38918349    COPD    View Evidence ○ I would code this ● I would need to check a reference first    ICD9(8) Reference Reason ○ Needs better documentation at point of care

| | Has | Needs | |
|---|---|---|---|
| | ☐ | ☐ | Current Status |
| | ☐ | ☐ | Treatment Plan |
| | ☐ | ☐ | Other |

○ Not a valid diagnosis
○ Valid diagnosis, but incorrect HCC

[ Submit ]    Next >

Fig. 13

Patient: 589037891-B

RAF Delta 0.41, Congestive Heart Failure (HCC 80), search 'cardiomyopathy' in the patient's record on Apixio to see clinical evidence for congestive heart failure. Consider ICD9 codes: 425.4, 425.1, 425.2, 425.3, 425.5, 425.7, 425.8 or 425.9

Background: *Cardiomyopathy was addresses in a face-to-face encounter as recently as 12/09/2010 but has not been claimed for 2010. Cardiomyopathy is relevant to HCC 80, Congestive Heart Failure.*

*All ICD9 Codes for HCC 80:*
402.01, 402.11, 402.91
404.01, 404.11, 404.91
415.0
416.0, 416.1, 416.8, 416.9
417.0, 417.1, 417.8, 417.9
425.1, 4252, 425.3, 425.4, 425.5, 425.7, 425.8, 425.9
428.0, 428.1, 428.20, 428.21, 428.22, 428.23, 428.30, 428.31, 428.33, 428.40
428.41, 428.42, 428.43, 428.9, 429.0, 429.1

Fig. 15A

[John Sample ✕ cardiomyopathy] [Search 🔍]

Patient Information
Name    John Sample
DOB     10/12/1943
Sex     U
Update Care Team
Invite to myApixio
Documents
Cardiology consult
coronary artery disease cardio

Upload Feed:
Ingrid Int

PSYCHOLOGICAL: Normal affect

LABORATORY AND DIAGNOSTIC DATA: EKG shows sinus bradycardia, intraventricular conduction defect. Nonspecific ST-T changes.

Laboratories noted with H&H 10/32 and white count of 7. INR 1.8. BUN and creatinine within normal limits. Cardiac enzyme profile first set 0.04, BNP of 10,000.

Nuclear myocardial perfusion scan with adenosine in the office shows ejection fraction of 30% with inferior reversible defect.

IMPRESSION: The patient is a 58-year-old gentlemen admitted for:
1. Pneumonia, chest x-ray confirms the same with shortness of breath.
2. Ischemic cardiomyopathy with abnormal stress test, inferior defect, ejection fraction 39% with elevated BNP, possibly secondary to underlying infection versus decompensated congestive heart failure.
3. Smoking history, hypertension, and hyperlipidemia.
4. Anticoagulation with Coumadin.

Fig. 15B

METHOD OF OPTIMIZING PATIENT-RELATED OUTCOMES

CROSS REFERENCE TO RELATED APPLICATION

This non-provisional application claims the benefit of provisional application No. 61/639,805 filed on Apr. 27, 2012, entitled "A Method of Optimizing Patient-Related Outcomes", which application is incorporated herein in its entirety by this reference.

This application is also a continuation-in-part application which claims the benefit of application Ser. No. 13/223,228 filed on Aug. 31, 2011, entitled "Medical Information Navigation Engine (MINE) System", which application claims priority to U.S. Provisional Application No. 61/379,228 filed on Sep. 1, 2010, of the same title, both applications are incorporated herein in their entirety by this reference.

BACKGROUND

The present invention relates generally to a medical information engine, and particularly to management and consolidation of medical information which enables computation of payoffs that track encounters.

Despite rapid growth of innovation in other fields in recent decades, the world of medical information, including patient medical records, billing, referrals, and a host of other information, has enjoyed little to no useful consolidation, reliability, or ease-of-access, leaving medical professionals, hospitals, clinics, and even insurance companies with many issues, such as unreliability of medical information, uncertainty of diagnosis, lack of standard, and a slew of other related problems.

One of the challenges facing those in the medical or related areas is the number of sources of information, the great amount of information from each source, and consolidation of such information in a manner that renders it meaningful and useful to those in the field in addition to patients. Obviously, this has contributed to increased medical costs and is perhaps largely attributed to the field suffering from an organized solution to better aid the medical professionals, to better aid those requiring more reliable patient history and those requiring more control and access over such information.

Currently, payoffs for medical encounters are not tied to the outcome. A physical therapy session is paid the same regardless of if the patient gains added function or not. This incentivizes providers to be inefficient, and prioritize quantity of care over the quality of care.

It is therefore apparent that an urgent need exists for a medical information navigation engine ("MINE") capable of managing medical information in a manner that is enables the calculation of payoffs in response to the outcome of an encounter. Such a system will increase care efficiency and increase care quality.

SUMMARY

To achieve the foregoing and in accordance with the present invention, systems and methods for managing medical information are provided. In particular, systems and methods for a Medical Information Navigation Engine ("MINE") is provided which can compare actual patient encounters with optimal encounters to generate a payoff.

In some embodiments, the system computes a current patient encounter vector for a current patient encounter, and then an optimal patient encounter vector is computed by assuming a best case patient encounter in accordance with the organizational objectives. The system is then able to compute the difference between the best case encounter and the current patient encounter. This difference is used to compute a corresponding payoff using an intelligent matrix.

In some embodiments, the patient encounter vectors and corresponding payoffs are collected to create a linear system. The linear system is optimized to obtain intelligence for the MINE. In some cases the difference between the optimal patient encounter vector and the current patient encounter vector is provided to a querying user and a querying electronic health record (EHR) system.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

In order that the present invention may be more clearly ascertained, some embodiments will now be described, by way of example, with reference to the accompanying drawings, in which:

FIG. 13 shows a screen shot of a specific opportunity finding with an exemplary interface of the way in which a user responds by providing feedback or validating the finding;

FIGS. 15A and 15B show examples of further details of the opportunity findings of FIG. 13.

DETAILED DESCRIPTION

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

As described in further detail below, the MINE 112, in an embodiment of the invention, computes future expected costs related to a patient, identifies groups (or "sets") of patients with similar situations and by reviewing lower and higher cost trajectories (or "projections"), identifies the "actions" that can be performed to allow patients or groups of patients to be moved into lower cost trajectory. "Cost" is merely one of a myriad of parameters taking advantage of the foregoing and in this respect any outcome of entry may be similarly improved. An example of an "action" is removing unnoteworthy gaps in documents, which results in an increase in revenue and lower costs.

Figure 1:
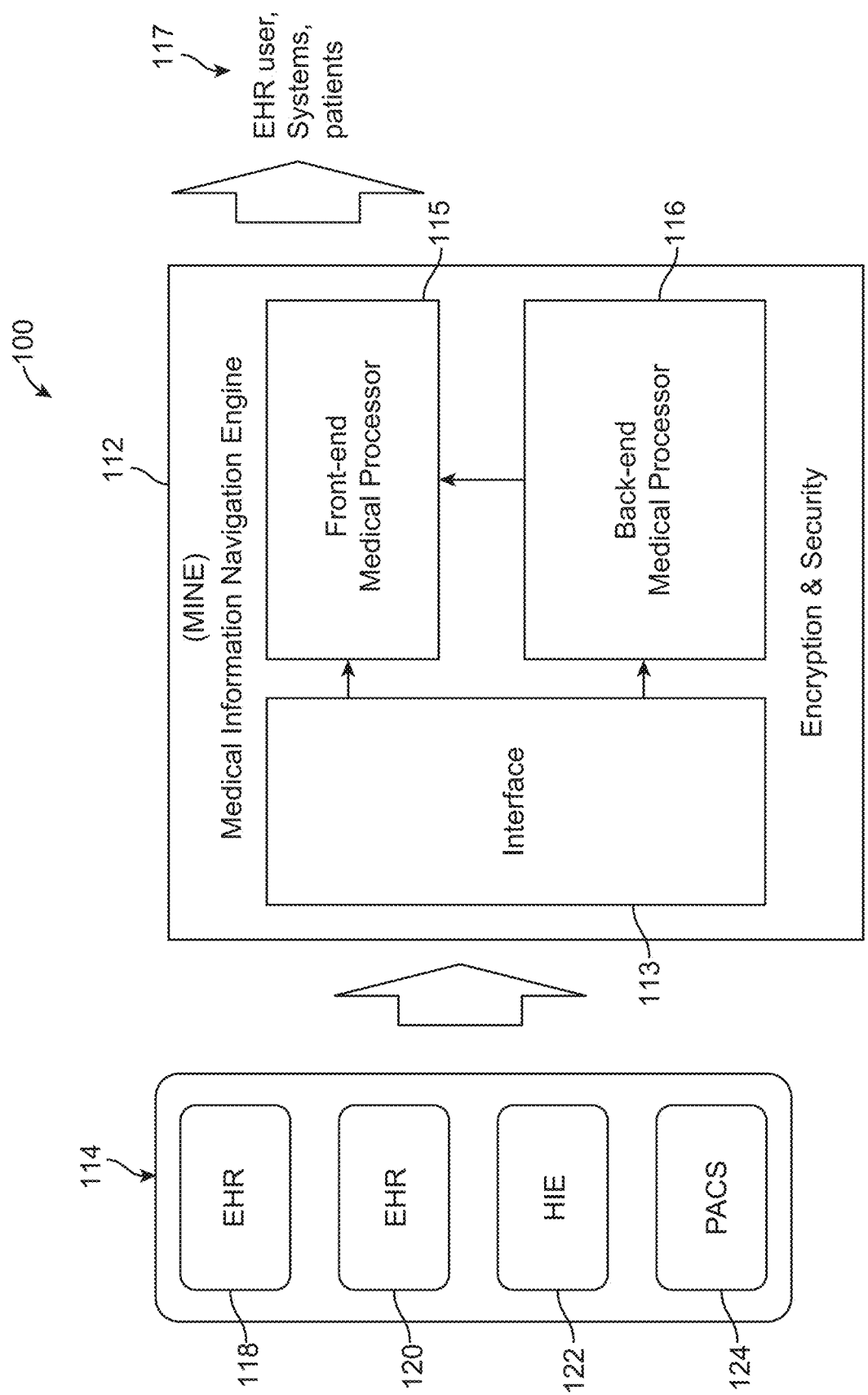
FIG. 1 shows a medical system 100, in accordance with an embodiment of the invention.

Referring now to FIG. 1, medical system 100, in accordance with an embodiment of the invention. The system 100 is shown to include medical source 114, a medical information navigation engine (MINE) 112, and medical information consumers (also referred to herein as "output" or "medical output") 117. The medical source 114 are shown to include an electronic health record (EHR) 118, EHR 120, health information exchange (HIE) 122, and a picture archiving and communication system (PACS) 124. The MINE 112 is shown to include interface 113, a back-end medical processor 116, and a front-end medical processor 115.

"Medical information", as used herein, refers to any health-related information, including but not limited to patient medical records, patient entered information, care team entered information, healthcare device generated information, and billing information.

The source 114 generally provides various medical information to the MINE 112. For example, the EHRs 118 and 120 each may provide information such as medical records and billing, the HIE 122 may provide information such as medical records, and the PACS 124 may provide information such as diagnostic imaging and reports.

The medical information consumers 117, which may be made of a host of entities or individuals, such as patients, clinics, medical institutions, health organization, and any other medical-related party, use information that is provided by the processor 115 of MINE 112 and that can, by way of example, consist of patients, medical systems, medical organization administrators, medical researchers, and/or EHR users. For example, user-customized processed medical information is provided by the processor 115 to a number of users within the medical information consumers 117. In this case, the processor 115 generates user-customized processed medical information to a plurality of users, with at least a portion of the user-customize processed medical information being provided to each of the users based on the relevancy of the portion being provided of each user's specific function or role and each user's associated security privileges.

The processor 116, in some embodiments, indexes identifies, maps, and consolidates medical information, received from the interface 113, and tags this information, and determines to reconcile the tagged information. In some methods and embodiments, information that is extracted from images is tagged to enhance recall of search queries. Indexing, at least in part, processes document and converts them into formats that allows for quick searching across a large collection of documents.

The information in the MINE 112 is encrypted and secure to ensure privacy of sensitive medical information.

It is understood that the sources 114 of FIG. 1 includes merely some examples of the sources that communicate with the MINE 112 and that other sources, known to those in the field, are contemplated. Similarly, the output 117 may be used by those or entities not discussed herein but that are contemplated and within the scope and spirit of the invention.

The interface 113 serves to receive information that is in various forms, such as but not limited to text, html, CCD, CCR, HL7 and any other type or formatted information. The interface 113 then provides to the processors 115 and 116 information, as needed.

The processor 116 receives some of the medical information that the interface 113 processes and performs certain tasks to process it, such as indexing, semantic meta-tagging, and reconciliation. Indexing takes processed documents and converts them into formats that make it easy to quickly search across a large collection of documents. Semantic meta-tagging embeds information into the medical information that is relevant thereto and that can be later used to search for certain information for the purpose of reconciliation and search, among many others.

One aspect of consolidation, reconciliation and de-duplication, generally refers to removing of redundant patient medical records, such as, multiple records for the same individual appearing as though the records are for different individuals or multiple data elements that are recorded similarly but slightly differently in the different sources. In this case, the processor 116 recognizes that the records belong to a single individual or are the same data and just recorded differently and automatically consolidates them. The patient or a user of the system 100 may also manually perform reconciliation. The processor 116 advantageously determines whether or not reconciliation is performed.

The processor 116 outputs the indexed, tagged and reconciled information to the processor 115. The foregoing tasks are a generalization and further details of each are provided below.

The processor 115 performs certain tasks on the information provided by the interface 113 and the processor 116, which include query, search, presentation, and quality checking. The output of the processor 115 is the output of the MINE 112, or output 117.

The MINE 112, through the processor 115, in some embodiments and methods, invites members of a medical care team to join it thereby allowing distributed user-organized care teams.

Querying, as performed by the processor 115, is the ability to receive, as input, a free text query, from a user, (i.e., a query without any restrictions on the structure)—and converting the free text query into commands to a medical search engine, such as Medical Lexical Search Engine and the MATRIX (Medical Application Terminology Relationship IndeX) Concept Search Engine, using a sophisticated query processing engine optimized to work with medical queries. The results of the search engine are sent to the presentation display planner—which decides the most relevant presentation given the user's organization and role (e.g., the provider, search query program, a healthcare administrator, a study administrator, and the patient). The presentation discussed below, receives such information. In some embodiments and methods, the medical information or user information is processed to suggest relevant queries.

Search, as performed by the processor 115, is built around the concept of Zero-Click Relevance—or the ability to get to all the relevant information an actor in the healthcare system requires by typing in just a single query. The search engine, within the processor 115, performing the search comprises an indexing and searching, as will become apparent shortly. Optionally, search results may be securely embedded into third party programs. In some embodiments, searching involves determining presenting (also referred to herein as "providing") access to specific relevant data based on a search query, the patient, and the user's specific function and/or role and security privileges. A user may be within the output 117 and security privileges are either determined by the MINE 112 or by the patient or both. The information that is uploaded to the MINE 112 by users, such as in output 114 (in some embodiments) is searched by the processor 115. The uploaded information may include information such as but not limited to status posts, records, and images. Such user-uploaded information is routed automatically to the output 117, as needed.

Some aspects of the search are now discussed relevant to an example. Assuming, by way of example, that Dr. Smith, an internal medicine physician, sees a new patient, Joan Sample, who presents with a complaint of chest pain. Joan has brought several continuity-of-care documents (CCDs) and a 600-page pdf file representing her medical chart. She has seen a cardiologist who uses NextGen's electronic medical record (EMR) and a gastroenterologist who uses eMD's EMR and she has recently visited a local emergency room. Dr. Smith uses the search of the various methods and embodiments of the invention to efficiently assemble the relevant information he needs. Dr. Smith selects Joan Sample as the patient and enters the clinical context "chest pain" in the search bar of a screen presented by the MINE 112 (examples of such screens are shown in subsequent figures herein). He is presented with relevant lab results, such as CKMB, troponin, and amylase, relevant diagnostic results, such as prior electrocardiograms (EKGs) and the most recent chest computed tomography (CT) scan; and all progress notes and consult reports in which concepts relevant to chest pain, like "GERD" and "cardiac stress test", are mentioned. Two distinct types of searches are combined, in accordance with a method and embodiment of the invention, to retrieve information medically relevant to Joan's complaint: 1) Lexical search, where text in the patient record is searched for occurrences of the search term, its variants and synonyms; and 2) Medical concept search, where data that is medically related to the search term is retrieved. Medical concept search finds relevant structured data with standardized codes, such as lab results, and text results, such as progress notes, which include terms medically related to the search term. In Joan's case, a search for "chest pain" returns a CKMB lab result and a reference to the most recent chest CT scan. Accordingly and advantageously, the Lexical and Medical concept search solves Dr. Smith's information overload problem by returning information in the chart most relevant to determining the etiology of Joan's chest pain complaint. Further, in some embodiments, the presentation, discussed shortly, presents a united view of Joan's history by reconciling and de-duplicating data from multiple sources that may be coded and described differently. Redundant data is automatically reconciled even if it is described differently by differently sources.

Presentation, as performed by the processor 115, is displaying health information to the requesting user in a way that reduces the number of clicks and maximizes the amount of meaningful information delivered based on the interpreting the intent of the user query.

Quality checking, as performed by the processor 115, is checking of the quality of medical information provided by various sources, i.e. source 114, by the patients, structured data, and unstructured data, in a Wiki-like mannered setting whereby the users can help maintain and improve the quality of information displayed. The foregoing tasks, performed by the processor 115, are further described in detail below. Additionally, the users or patients may make comments regarding medical information, in a Wiki-like manner.

In summary, the MINE 112 transacts medical information including the interface 113 receiving medical information from a number of medical sources (such as within the source 114) for processing, identifying, mapping, and consolidating by the medical processor 116, providing access to specific relevant data, based on a user's security privileges, within the identified, mapped, and consolidated medical information, based on user-specific functions or roles, performed by the processor 115, and generating user-customized processed medical information to a number of users, such as within the output 117, with at least a portion of the user-customized processed medical information being provided to each of the users based on its relevancy to each user's specific function or role and each user's associated security privileges.

Figure 2:
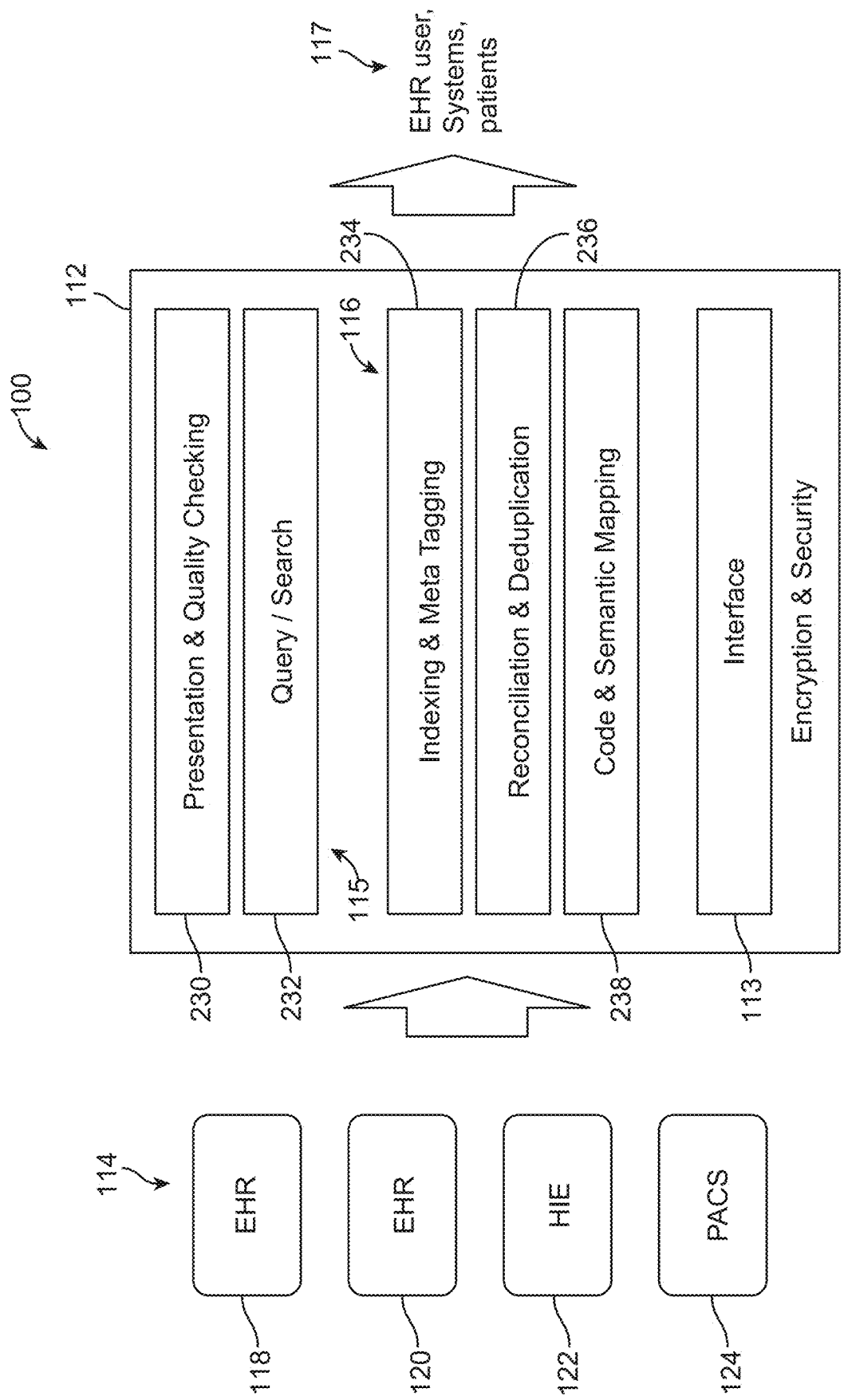
FIG. 2 shows further details of the system 100, particularly the MINE 112 thereof.

FIG. 2 shows further details of the system 100, particularly the MINE 112 thereof. That is, the processor 116 is shown to include an indexing and meta tagging module 234, which includes an indexing module and a meta tagging module (both of which are not shown in FIG. 2 in the interest of clarity), which may be a module, as shown in FIG. 2 or two physically separate modules. The processor 116 is further shown to include a reconciliation and de-duplication module 236, which also can be broken out into two modules, a reconciliation module and a de-duplication module, and a code and semantic mapping module 238, which also may be a single module or multiple modules. The modules 234, 236, and 238 communicate with one another.

The processor 115, in some embodiments, includes display and visualization 340 executing on one or more servers 238, which may be any suitable computing engine, similar to the servers 232, including but not limited to PCs or servers. The display 340 is used to construct presentation and display information to users, such as the patient's records, billing information, and other types of medical information. The display 340, in some embodiments, also performs processing of some of the functions of the processor 115.

The foregoing modules may be software programs, executed by a computer or computing engine of suitable sorts, or may be implemented in hardware.

Figure 3:
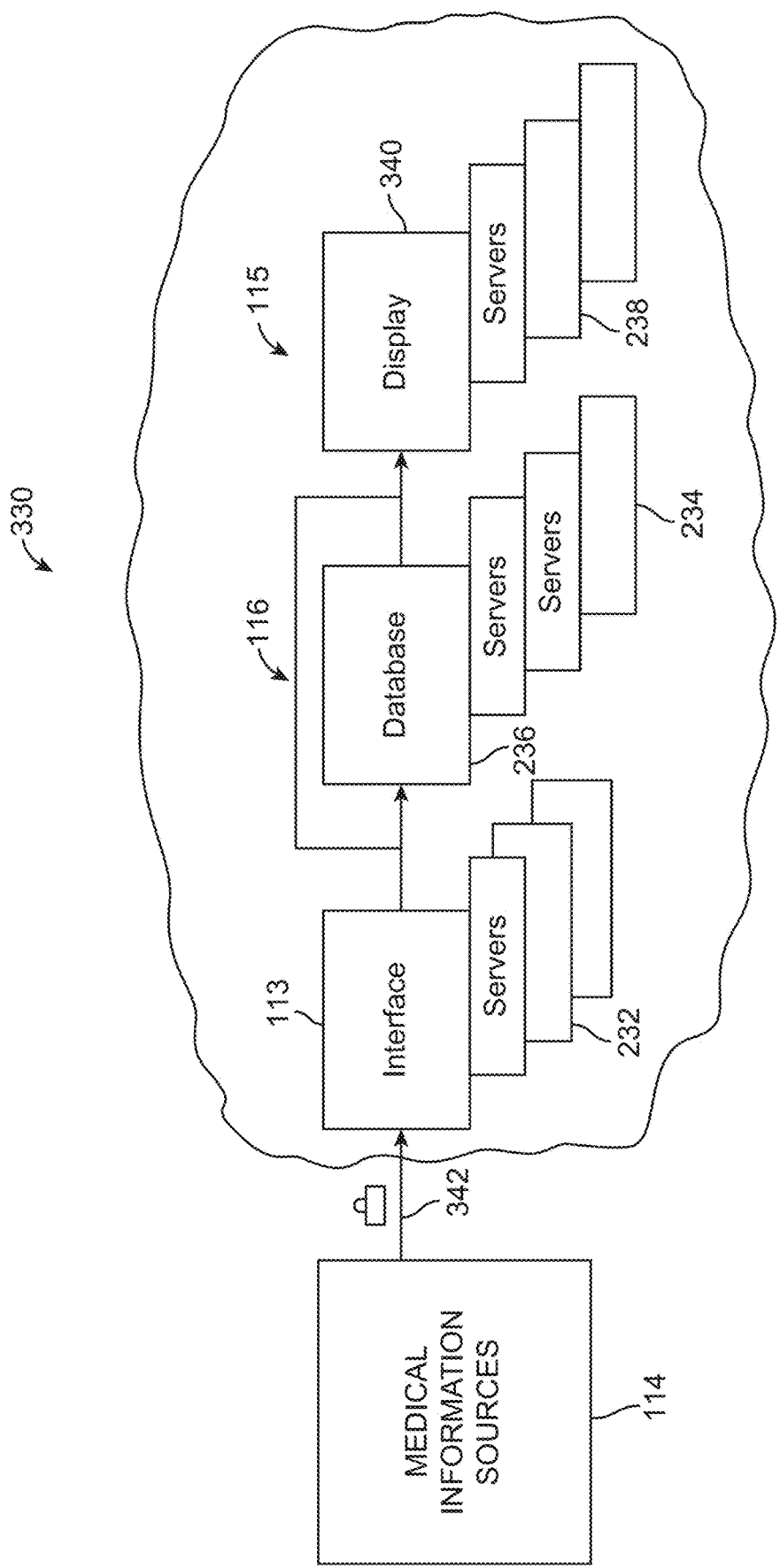
FIG. 3 shows an exemplary embodiment implementing the system 100 using various devices.

FIG. 3 shows an exemplary embodiment implementing the system 100 using various devices. That is, the medical system 330 is analogous to the system 100 and is shown to include the sources 114 coupled to communicate, securely, through the secure communication link 342, to the interface 113. The link 342 may be any suitable communication channel allowing information, of various formats and types, to be transferred to the interface 113 in a secure and encrypted fashion. Exemplary communication channels of which the link 342 is made include the Internet, VPN connections over the Internet, private dedicated digital lines such as T1, T3, E1, E3, SONET, and other fiber optic formats.

The interface 113, in some embodiments, is a software program that executes on one or more servers 232, which can be a server of any kind of suitable computing engine, such as personal computer (PC). The servers 232 receive secure information through the link 342 from the sources 114. The processor 116, in some embodiments, includes the module 236 and one or more servers 234, which may be any suitable computing engine, similar to the servers 232, including but not limited to PCs or servers.

The module 236 and servers 234 perform the tasks discussed above relative to the processor 116 and the display 340 and servers 238 perform the tasks discussed above relative to the processor 115 though these processors may and often perform additional tasks related to medical information, some examples of which are presented and discussed below and the rest of which are contemplated and achieve the various advantages, results and functions presented herein.

The processor 115, in some embodiments, includes display and visualization 340 executing on one or more servers 238, which may be any suitable computing engine, similar to the servers 232, including but not limited to PCs or servers. The display 340 is used to construct presentation and display information to users, such as the patient's records, billing information, and other types of medical information. The display 340, in some embodiments, also performs processing of some of the functions of the processor 115.

As shown in FIG. 3, the servers 232 are coupled to the module 236 and the servers 234, and to the display 340 and the servers 238 and the module 236 and servers 232 are coupled to the display 340 and the servers 238.

In some embodiments, the interface 113, servers 232, module 236, servers 234, display 340, and servers 238 are remotely located relative to the sources 114 and in some embodiments, remotely located relative to one another. Further, they are considered a part of the Internet cloud where, performing their tasks in a manner known as "cloud-computing". However, other manner of achieving the functions and advantages of the invention, including various other of implementation, not shown in FIG. 3 or other figures herein and/or not discussed are contemplated.

Figure 4:
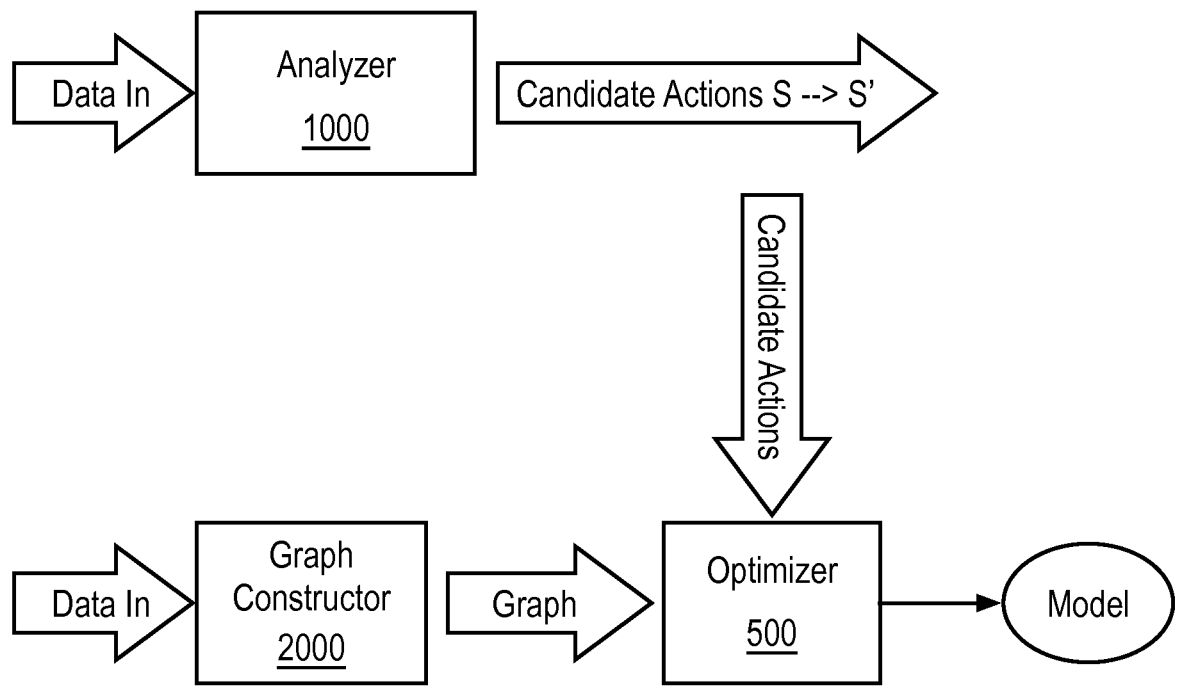
FIG. 4 shows an analyzer system 499, in accordance with a method and embodiment of the invention.

FIG. 4 shows an analyzer system, in accordance with a method and embodiment of the invention. The system is shown to include an analyzer 1000, a graph constructor 2000, and an optimizer 500. The system is included as a part of block 116 of FIG. 1 and block 234 of FIG. 2.

The analyzer 1000 is shown to generate candidate actions, which are employed by the optimizer 500. The analyzer 1000 identifies which state transitions (S1—>S2) are actions and which can be applied in the model-building step (system 500) to optimize for the desired outcome. In one version, concepts are identified as actions (as opposed to, for example, events or other non-modifiable outcomes) based on their classifications in medical ontologies (Systematized Nomenclature of Medicine-Clinical Terms (SNOMED CT) for example, others can be found in Unified Medical Language System (UMLS) and National Center for Biomedical Ontology (NCBO)). In another version, the graph constructor 2000 is used to generate a graph, and then specific state transitions that modify the expected future outcome (e.g., NPC) can be identified.

The optimizer 500 performs global optimization for a cohort of patients, which is also to construct an action suggestion model. Identification of optimal "actions" for a single patient or patient state timeline is optimized globally over a cohort of patients for multiple events of interest. Such an optimization can be computed for a particular care delivery environment, taking into account resource constraints and complex interactions between different actions and state patterns. The globally optimized actions that result from this optimization process are applicable to many healthcare delivery scenarios including Accountable Care Organizations (ACOs) and other at-risk payment models, healthcare payers, healthcare systems and even individual hospitals that must optimize readmission rates and other outcomes.

One method of performing the foregoing optimization is to identify a set of events of interest, compute the health correlation graph for all events of interest for all patients in the system to be optimized and then compute a global figure of merit for the system. The figure of merit can be any function of the impact value and time, computed over the entire patient cohort. One example of a figure of merit is the expected cost of care per unit of time for the entire cohort or projected cost of care (or NPC) over some future time window.

The global figure of merit is optimized using standard techniques for large data analytics for variations in the actions taken at each event of interest. Since each action locally optimizes the future path of the patient, the global optimum for all possible actions will include complicated interactions between actions and will result in an optimization strategy that improves outcomes at the global or system-wide level, rather than just the local optimization for a single patient for a single event of interest. The properties of the system to be optimized can be represented as constraints in this analysis so that unrealizable actions are not suggested by the optimized model. This process results in an optimized action suggestion model. An important advantage of the action suggestion model is to suggest actions which optimize over expected future outcomes for the individual and the cohort, conditioned upon the likelihood that the action will be taken and will have the desired effect.

Figure 5:
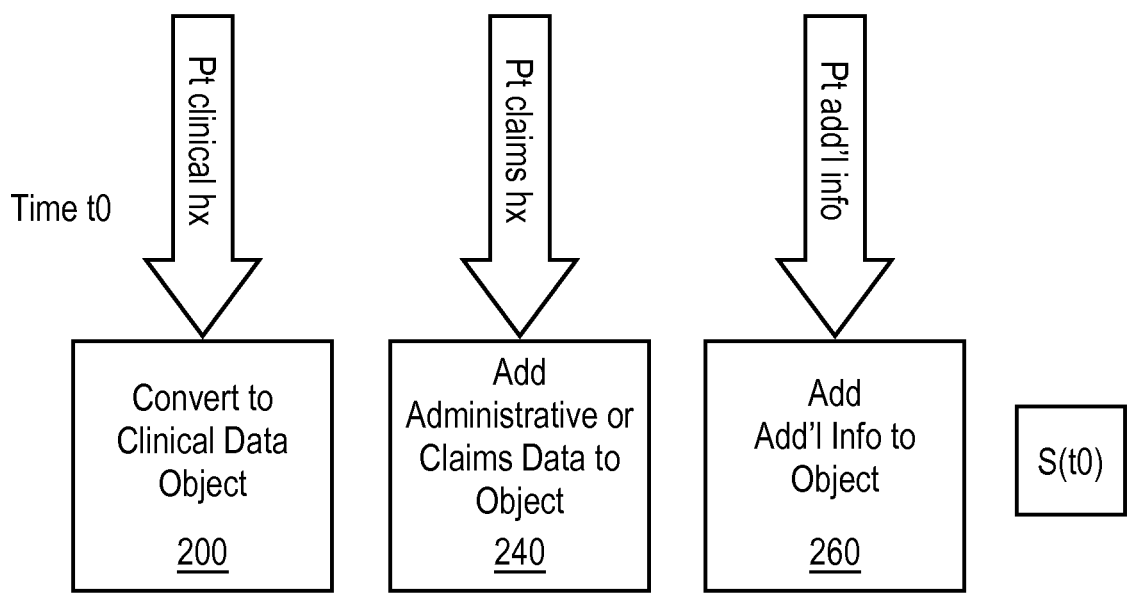
FIG. 5 shows a patient clinical history system, in accordance with an embodiment and method of the invention.

FIG. 5 shows a patient clinical history system, in accordance with an embodiment and method of the invention. Patient clinical history, at 200, is converted to a data object in the following manner. It is understood that the embodiments of FIGS. 1-3 perform the steps of FIGS. 4 and 5. Concepts are extracted from narrative and structured data. Presence or absence in the chart for each concept can be noted as a binary or the set of applicable concepts can be retained as a set. Measurements, in some embodiments and methods, are documented in any combination of ways, including presence/absence of the measurement, a list of measurements, each measurement including a date, value, and additional metadata. The most recent measurement, an enumeration of whether the most recent measurement was high, low, abnormal or normal, a windowed listing of high/low normal for most recent N measurements, and the like. Depending upon the application, concepts from different sources (different care environment, different types of source document, and the like) may be separated into different sections in the state object.

At step 240, patient claims history is constructed analogously to step 200 except that only procedures, problems and medications are enumerated in the history data object. Either current medications or current and past medications can be included, depending on the application. At step 260, additional patient information is added to the patient data object. Additional information includes but is not limited to current employment status, income level, disability status, distance to nearby healthcare facilities, demographic information, such as but not limited to address and gender, patient compliance history, self reported status, and the like.

S(t0), the patient object, results from the process of FIG. 5 and describes the patient's "state" at time t0.

Figure 6:
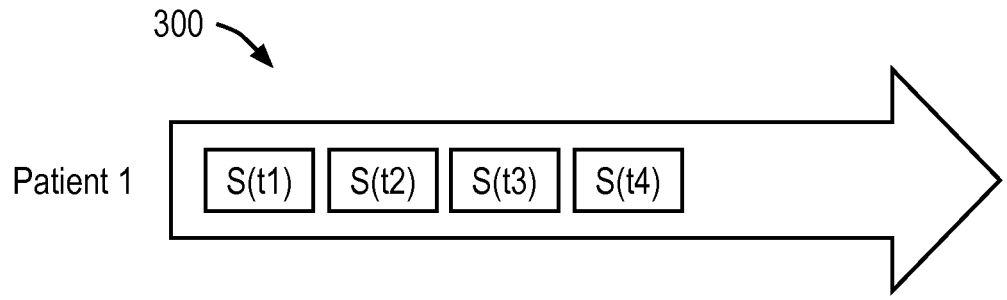
FIG. 6 shows the construction of a patient state timeline 300, in accordance with a method of the invention.

FIG. 6 shows the construction of a patient state timeline 300, in accordance with a method of the invention. The construction is performed by ordering individual states, such as S(t1), S(t2), S(t3), and S(t4), in time order. S(t1), S(t2), S(t3), and S(t4) each represent a patient state at a particular time. For example, "S(t1)" represents a patient state at time "t1".

Figure 7:
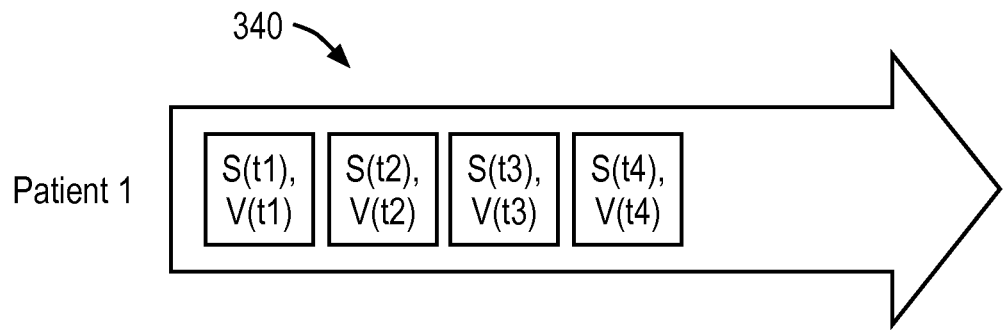
FIG. 7 shows the addition of impact measures, V(t), to the patient state timeline of FIG. 6.

FIG. 7 shows the addition of impact measures, V(t), to the patient state timeline of FIG. 6. At 340, in FIG. 7, impact measure, V(t), is shown to be associated with each of the patient states of the timeline of FIG. 6. For example, the impact measure V(t) is the cost of services provided at time t2, the change in any measurement associated with a transition from state S(t1)—>S(t2). Exemplary measures include but are not limited to expected outcome, time spent to manage patient care, resources consumed in any part of the system, and the like.

Computation of expected future impact can be computed at any time, for example t2, by adding the values of V for all future nodes (t>t2) on the patient state timeline of FIG. 7. An alternative method is to compute the net present value of the series of future V values by discounting future values by an effective discounting rate. A specific example of this is the Net Preset Cost ("NPC") determined by computing the sum of discounted costs (V(t)=cost at node t) for future times.

Figure 8:
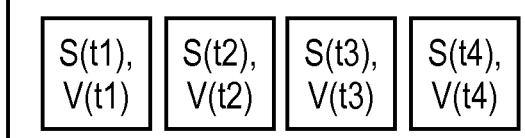
FIG. 8 shows associated or correlated states identified between patients forming a set of patients.
Figure 8:
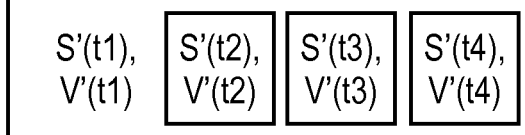

FIG. 8 shows associated or correlated states identified between patients forming a set of patients. At 360, it is evident that a degree of association between two patient states or two subsets can be computed on the patient state timelines of different patients. "Association" can be thought of as a distance or level of relatedness. For example, the cosine angle between two states, computed from an inner product between the states, is a measure of association or similarity. Such an inner product can be computed on the projection of two states onto a subspace of the state space as well. In general, associations between states can depend on the application. For example, in some applications, any two states that include a new diagnosis of diabetes (of any kind) might be considered to be "near" each other, while a specific series of events or states might be required for nearness in another application.

Figure 9:
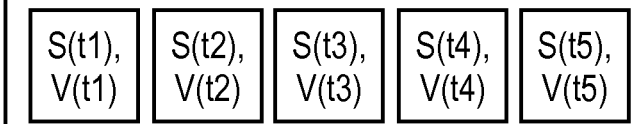
FIG. 9 shows the generation of a composite patient state timeline 380 from the patient state timelines of multiple patients, in accordance with a method of the invention.
Figure 9:
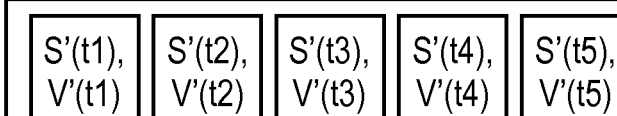
Figure 9:
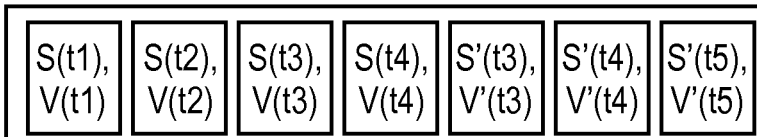

FIG. 9 shows the generation of a composite patient state timeline 380 from the patient state timelines of multiple patients, in accordance with a method of the invention. In accordance with the method of FIG. 9, if the duration of history that is needed for a particular application is longer than the available data, then it is possible to use associated states or associated state sub-patterns to merge multiple patient state timelines into a composite. Alternatively, a composite patient history is created based on age so that longer patient histories, spanning a longer age range, can be computed from a dataset of shorter duration. In the general case, composite patient state timelines are created from patient state timelines which exhibit similarities, correlation, association, or nearness in a space of interest (such as joining at a similar point or on similar subset).

Figure 10:
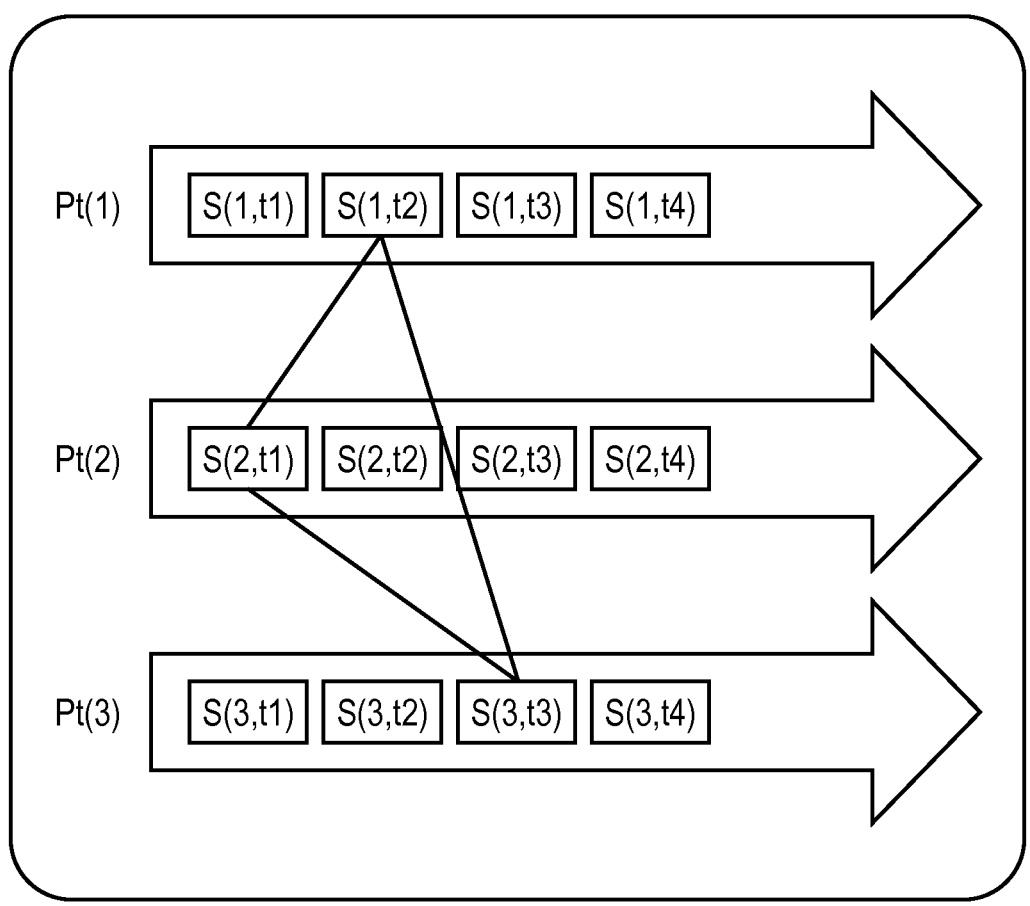
FIG. 10 shows construction of health correlation graph ("HCG") 400 for a particular application, in accordance with another method of the invention.

FIG. 10 shows construction of health correlation graph ("HCG") 400 for a particular application, in accordance with another method of the invention. The HCG of FIG. 10 is constructed by identifying one or more events of interest, such as a state or state pattern. All patient state timelines that exhibit such events of interest are aligned at the time (tx) that the event occurs. Once the patient state timelines are aligned, a distribution of future impacts or discounted future impacts (such as NPC) is computed from impact values, V(t), for t>tx (or for a time window such as tx<t<tmax). Such a distribution can represent the future cost of caring for a cohort of patients, the future risk of specific outcomes for a cohort of patients, or many other values of interest.

Analysis of the distribution of future impacts, such as sorting, clustering, sensitivity analysis, correlation analysis, spectral decomposition, and the like, can be sued to identify actions that impact future outcomes. An exemplary application of this analysis is the identification of actions that can be taken to optimize future risk, cost or other impact for a patient, given a particular state or patient state timeline. Recommended actions can include healthcare provider actions, such as performance of a particular diagnostic or particular treatment, care manager actions such as initiating a particular intervention or scheduling a patient visit, a patient action such as change in diet or activity pattern or a measurement such as body weight or blood pressure, or it can be an action to be carried out by a care provider or other community resource. Such business intelligence is of high value to healthcare systems, payers and patients.

Figure 11:
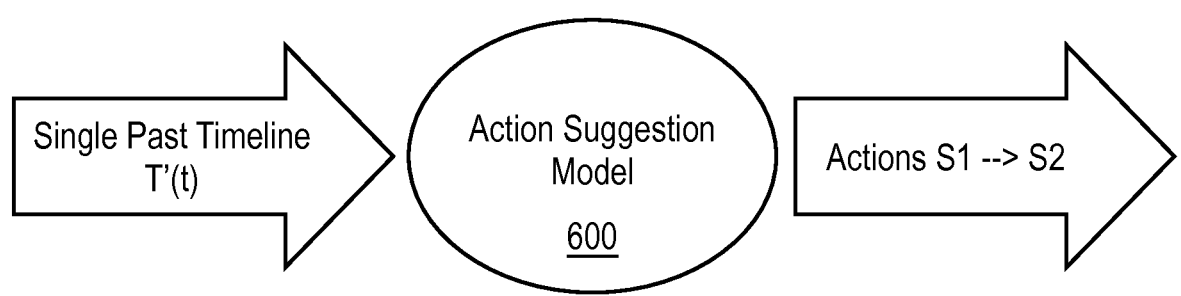
FIG. 11 shows an application of an optimized action suggestion model once the action suggestion model has been constructed.

FIG. 11 shows an application of an optimized action suggestion model once the action suggestion model has been constructed. The action suggestion model can be then applied to a single patient state timeline to suggest a ranked list of appropriate actions for that patient. Actions represent state transitions which lead to better outcomes for the patient and for the cohort as a whole, given the properties of the system.

In summary, an exemplary method is disclosed for constructing a "Patient State Vector" (mathematical representation of the current state of the patient health, including their complete history) for at least one patient that comprises clinical history and additional factors (demographics, economics, location, past social behavior, social network data, self reported status, inferred patient compliance patterns, genetic data,) that represents the patient's "state" at a single point in time.

Also, a method is disclosed for tracking the evolution of the "Patient State Vector" across time and constructing a time series (or graph) of Patient History Vectors that represents the patient's "health trajectory".

The association of costs or impacts for various state transitions (changes from one state to another) is made for the purpose of computing net present cost ("NPC"), projected cost, actual cost, risk of cost or other objective.

Further, composition of multiple patient trajectories for patients of different ages is disclosed to create longer effective trajectories from data of limited historical duration. Points of concatenation of such trajectories can be based on similarity associations as described above.

Moreover, an association is created between the states of two different patients which represent a particular kind of similarity or correlation between the patient states. Such an association can be based on correlation, vector cosine angle in the space of states, clustering of patients within the space of states, "distance" between the two points in the space of states, common pattern in state or subset of states (DC-BA→CBA) etc.

A "health correlation graph" is generated by making such associations among multiple patients of interest.

A spectrum or probability distribution of future trajectories or outcomes (either representing each entire path or the NPC or impact function) is also generated starting from a common state or event.

Actions are identified which can change the likelihood of a particular future trajectory or NPC.

Such actions are inclusive in an optimization over a population of patients (such as those cared for by a particular healthcare system) to globally optimize a desired outcome (NPC, safety, quality of life measure, etc.) to create suggested actions based on not only the likely ideal impacts of these actions but the probability that the actor (provider, care manager, healthcare provider, patient) will take the suggested action.

A graph is generated of patient state changes, including possible optional actions, and compute NPC or other objective value for each node in graph. Optimization is done to determine projected outcome (cost) and possible actions to modify (improve) outcomes.

A method and system to construct a patient history vector (mathematical representation) is disclosed for at least one patient that comprises a projection of clinical history and additional factors (demographics, economics, location, past social behavior, social network data, self reported status, inferred patient compliance patterns) that represents the patient's "state" at a single point in time onto a subspace that reduces noise and improves accuracy of predictions and effectiveness of suggested actions.

In another method of the invention, a determination is made of a set of patients of interest to include in an optimization for a particular objective. For example, patients with diabetes and hypertension who live within a particular distance from a primary care center and who have exhibited a particular past compliance characteristic are compiled into such a set of patients of interest. One method to determine patients of interest is to identify portions of the "health correlation graph" with particular mathematical properties such as connectedness, density of connections, average NPC, etc.

Figure 12:
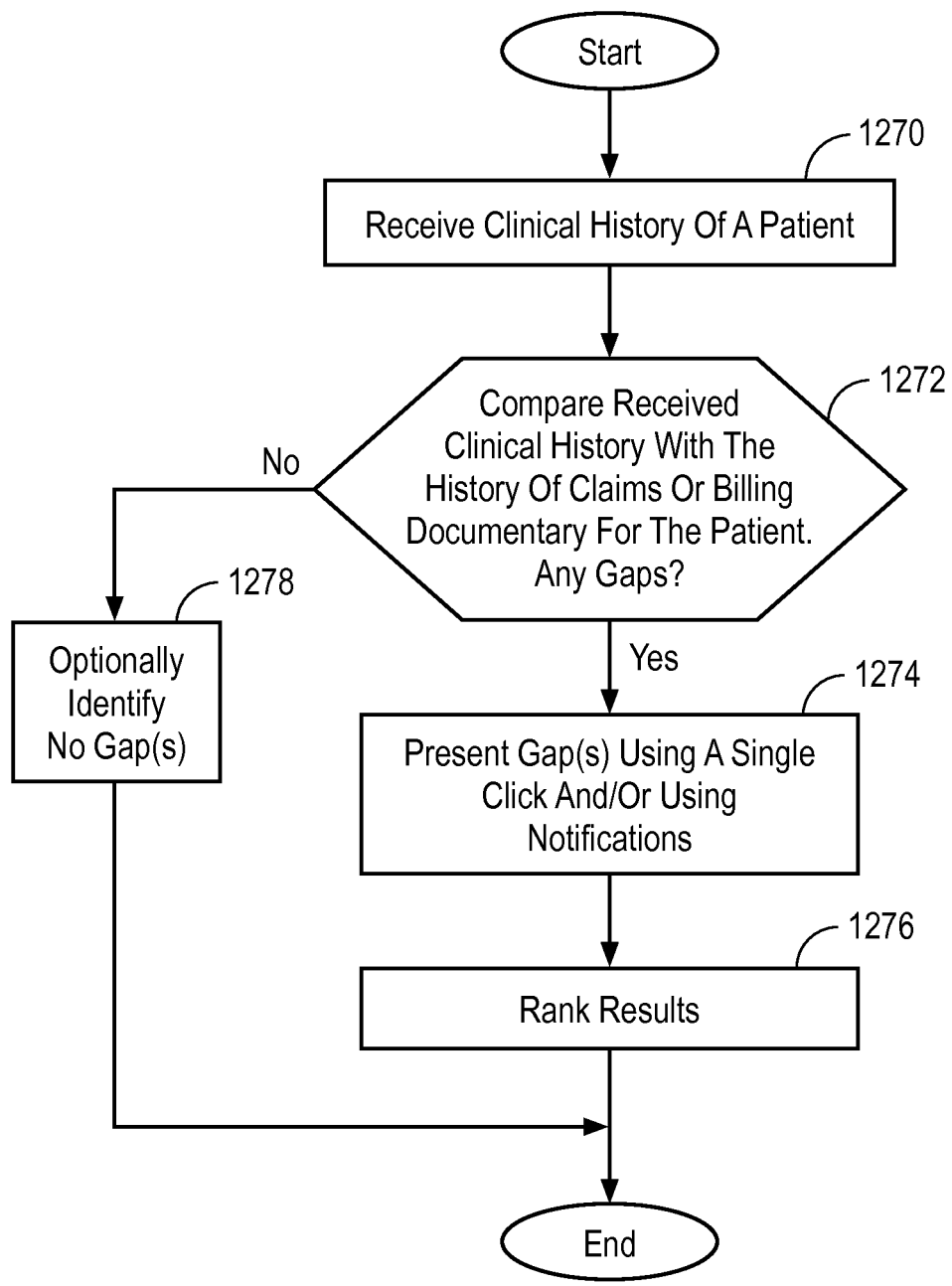
FIG. 12 shows a flow chart of the steps performed by the block 16 of FIG. 1 to identify gaps between clinical documents and the billing process of a healthcare organization.

In accordance with another method, FIG. 12 shows a flow chart of the steps performed by the block 116 of FIG. 1 to identify gaps between clinical documents and the billing process of a healthcare organization. The method starts at step 1270 by receiving clinical history of a patient. Next, at 1272, the received clinical history of the patient is compared with the history of claims or billing documentation, the latter having been saved. An exemplary process using the method of FIG. 12 is for identifying medical conditions and services of interest within a period of interest and comparing them to medical conditions or services documented within a billing system to identify gaps and/or discrepancies.

If at 1272, the comparison yields one or more gaps, the process continues to step 1274, otherwise, step 1278 is performed. At step 1274, the identified gaps are presented, in one method of the invention, in a way that a single click can lead to examination of the clinical evidence. In accordance with another method of the invention, gaps are presented as notifications to users in specific situations (specialty, care setting, patient comorbidities, etc.). Such notifications can include specific instructions for users for how to correct for the gap or discrepancy.

Gaps can also be rated or commented on as a way to improve the method and validate findings. After step 1274, at step 1276, results from step 1274 are ranked based in information flow and friction on the system under investigation to optimize the impact of individual actions. An additional application of this method is the identification of level and quality of documentation of clinical findings, diagnoses, procedures, etc.

If at 1272, no gaps are identified, optionally, this is noted at step 1278.

These methods can be used for the purposes of HCC coding, auditing, improvement of quality of services provided, process assessment, process change, quality of documentation, improving reimbursement, reducing patient risk, and improving care of the patient.

More specifically, a patient state timeline is generated using ICD-9 concepts (shown in FIG. 5) (or other coding system, such as ICD-10, for time periods in which Medicare Advantage requires such coding system) in which each event is a clinical encounter that has been submitted for reimbursement. Each state vector consists of multiple sections, corresponding to concepts found in encounter note sources, other clinical sources, and administrative and claims data sources. The encoding for the HCC application is binary values indicating presence or absence of every concept in the coding system of interest (e.g., ICD-9). As a computational convenience, sections for cross-terms between all the concepts in the state vector are also included, to create a final input vector X which contains both state and cross-term information.

Data for all patients is combined into a single timeline, the "aggregated timeline" (an example of which is shown in FIG. 9), by taking the union of all state vectors and events and sorting them in time order. Ordering for different patient events on the same day is resolved randomly since this level of ordering does not affect results.

The outcome value, V, for each encounter is the Medicare Advantage RAF score attributable to that visit.

A vector of model weights w is computed by solving the equation:

$$wX = V \qquad \text{Eq. (1)}$$

where 'V' is the vector of outcomes for each event in the aggregated timeline.

The resulting vector, 'w', can be interpreted as the incremental contribution to the final RAF score from a particular appearance of a concept in a particular part of a patient's history.

Figure 14:
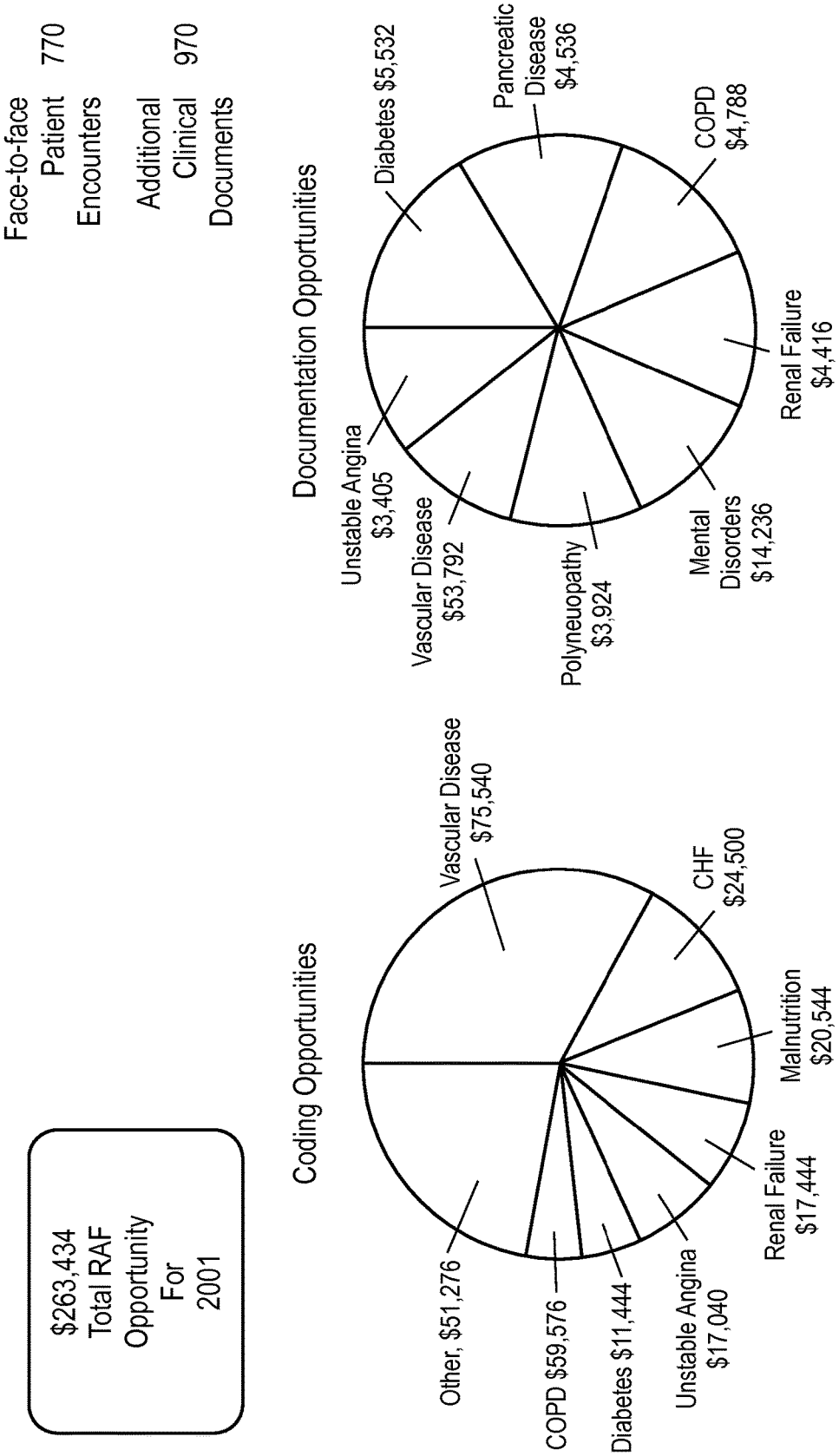
FIG. 14 shows an example of the summary of the findings of FIG. 13.

Concepts in the encounter and other clinical portions of the state vector for each patient (i.e., not claims data or cross-terms) are mapped to the HCC coding hierarchy and then compared against the HCC codes that were actually claimed. These are the HCC opportunity findings. FIG. 13 shows a screen shot of a specific opportunity finding with an exemplary interface of the way in which a user responds by providing feedback or validating the finding. FIG. 14 shows an example of the summary of the findings of FIG. 13. FIGS. 15A and 15B show examples of further details of the opportunity findings of FIG. 13. The highlighted language of FIGS. 15A and 15B is used as a link to an application for facilitating the single click gap presentation discussed above.

Multiplying these concepts by their weights in the w vector then gives a measure of the expected impact of the finding on the final RAF score. This measure is used to rank the HCC opportunity findings so that they can be acted on in an optimal order.

Analysis of the weights of the model and the HCC opportunity findings yields other results as well, such as which codes are most likely to lead to reimbursement, and where the "friction" for information flow in the system is high.

Although the invention has been described in terms of specific embodiments, it is anticipated that alterations and modifications thereof will no doubt become apparent to those skilled in the art. It is therefore intended that the following claims be interpreted as covering all such alterations and modification as fall within the true spirit and scope of the invention.

What is claimed is:

1. In a Medical Information Navigation Engine ("MINE"), a computerized method for knowledge extraction and exchange, the method implemented by at least one processor of the MINE, the method comprising:

receiving, by the at least one processor from a plurality of medical data sources, medical information for a plurality of patients, the medical information received in various formats;

converting, by the at least one processor, the medical information into a format to facilitate search speed for data queried from the medical information;

generating, by the at least one processor and using the converted medical information, a plurality of patient state timelines, wherein each patient state timeline corresponds to a particular patient of the plurality of patients, and wherein each patient state timeline is an ordering of individual states in a time order;

generating, by the at least one processor, a plurality of impact measures for each of the plurality of patient state timelines, wherein each impact measure is a cost of services provided at a given time to transition from one state to another;

identifying, by the at least one processor, a state of interest in a subset of the plurality of patient state timelines;

aligning, by the at least one processor, the subset of the plurality of patient state timelines at a time when the state of interest occurs;

summing, by the at least one processor, all impact measures after the state of interest occurs for each of the subset of the plurality of patient state timelines to generate a probability distribution of future impacts;

generating, by the at least one processor, a suggestion model by analyzing the distribution of future impacts to select actions that change a likelihood of a future outcome that maximizes at least one organizational objective, wherein the at least one organizational objective includes safety, quality of life measure and reduction of net present cost; and applying, by the at least one processor, the suggestion model to one patient state timeline to generate recommendations for the corresponding patient.

2. The method of claim 1 wherein the generating the probability distribution utilizes a clinical history, wherein the clinical history is supplemented by at least one additional factor including demographics, economics, location, past social behavior, social network data, self-reported status, and inferred patient compliance patterns.

3. The method of claim 1 wherein the actions are at least one of a healthcare provider action, a care manager action, and a patient action.

4. The method of claim 3 wherein the identified healthcare provider action includes performance of a diagnosis of or a treatment for the corresponding patient.

5. The method of claim 3 wherein the identified care manager action includes initiating an intervention or scheduling a patient visit.

6. The method of claim 3 wherein the identified patient action includes at least one of a change in diet or activity pattern, and a measurement of a body weight or a blood pressure.

7. The method of claim 1 further comprising applying the suggestion model to each of the subset of the plurality of patient state timelines to generate a set of actions for a cohort.

8. The method of claim 7 further comprising optimizing all the actions for the cohort to identify globally optimal actions for the cohort.

9. The method of claim 8 wherein the optimizing includes computing a global figure of merit function of impact to a desired outcome and time for the cohort.

10. The method of claim 1 wherein the actions include removing at least one gap in a medical document, wherein the at least one gap is a discrepancy between an identified medical condition or service and medical condition or service documented in a billing system.

* * * * *